(12) United States Patent
Maughan et al.

(10) Patent No.: US 7,033,620 B2
(45) Date of Patent: Apr. 25, 2006

(54) PRODUCT AND PROCESS FOR STABILIZING ALOE VERA GEL

(75) Inventors: Rex G. Maughan, Paradise Valley, AZ (US); Roger A. Poore, Rockwall, TX (US); Ben V. Phan, Garland, TX (US)

(73) Assignee: Aloe Vera of America, Inc., Dallas, TX (US)

( * ) Notice: Subject to any disclaimer, the term of this patent is extended or adjusted under 35 U.S.C. 154(b) by 52 days.

(21) Appl. No.: 10/448,044

(22) Filed: May 28, 2003

(65) Prior Publication Data

US 2003/0211182 A1 Nov. 13, 2003

Related U.S. Application Data

(62) Division of application No. 10/116,364, filed on Apr. 4, 2002, now Pat. No. 6,713,095.

(51) Int. Cl.
A01K 35/78 (2006.01)

(52) U.S. Cl. ....................................... 424/744; 424/725
(58) Field of Classification Search .............. 424/195.1, 424/725, 744
See application file for complete search history.

(56) References Cited

U.S. PATENT DOCUMENTS

| | | | |
|---|---|---|---|
| 3,892,853 A | 7/1975 | Cobble | |
| 4,178,372 A | 12/1979 | Coats | |
| 4,446,131 A * | 5/1984 | Maughan | 424/744 |
| 5,356,811 A | 10/1994 | Coats | |
| 6,245,377 B1 | 6/2001 | Tao | |
| 6,261,603 B1 | 7/2001 | McElwain | |
| 6,713,095 B1 | 3/2004 | Maughan et al. | |
| 2002/0192346 A1 | 12/2002 | Cavazza | |
| 2003/0007961 A1 | 1/2003 | Wilburn | |
| 2003/0211181 A1 | 11/2003 | Maughan et al. | |

OTHER PUBLICATIONS

Carattini, L. Health Benefits of Green Tea; PageWise Web p. 2002 URL <http://vtvt.essortment.com/greenteaheal_rbdy.htm, accessed Aug. 31, 2004.*

Nutrition Facts: URL <http://www.food-stats.com/Fruits_and_Fruit_Juices/Grapes_red_or_green_european_type_varieties_such_as_Thompson_seedless_raw-.html>, accessed Aug. 31, 2004.*

Polyphenolics, Inc., "The Health Benefits of MegaNatural Gold," (author and date unknown).

Polyphenolics, Inc., "MegaNatural Gold (Grape Seed Extract) Technical Publication I," (author and date unknown).

Eastman Chemical Company, "Frequently Asked Questions About NuTriene Tocotrienols," publication V–24, Feb., 1998, (author unknown).

* cited by examiner

Primary Examiner—Patricia Leith
(74) Attorney, Agent, or Firm—Scott T. Griggs; Griggs Bergen LLP

(57) ABSTRACT

A product and process for stabilizing Aloe vera gel is disclosed. The process includes the steps of rapidly heating the Aloe vera gel to a temperature in the range of from about 35° C. to about 80° C., adding to the heated Aloe vera gel one or more stabilizing antioxidants, and rapidly cooling the heated Aloe vera gel to a temperature in the range of from about 20° C. to about 30° C. The stabilizing antioxidants may be a tocotrienol/tocopherol blend, rosmarinic acid, polyphenols, or any combination thereof.

23 Claims, 3 Drawing Sheets

PRODUCT AND PROCESS FOR STABILIZING ALOE VERA GEL

CROSS-REFERENCE TO RELATED APPLICATION

This is a divisional application of U.S. patent application Ser. No. 10/116,364, entitled "Product and Process for Stabilizing Aloe Vera Gel," filed on Apr. 4, 2002 now U.S. Pat. No. 6,713,095, in the names of Rex G. Maughan et al. This application discloses subject matter related to the subject matter disclosed in co-pending U.S. patent application Ser. No. 10/447,970, entitled "Product and Process for Stabilizing Aloe Vera Gel," filed on May 28, 2003, in the names of Rex G. Maughan et al.

TECHNICAL FIELD OF THE INVENTION

This invention relates to the processing of Aloe vera gel, and more particularly to a product and controlled temperature process in which antioxidants and other stabilizing agents are used to stabilize the Aloe vera gel.

BACKGROUND OF THE INVENTION

Aloe vera is a tropical or subtropical plant of the lily (Liliaceae) family that has leaves growing in a spiral rosette pattern around a central stem. The leaves of the Aloe vera plant contain a viscous but essentially clear gel given structural rigidity by hair-like connective fibers that run therethrough. Freshly excised from the plant, Aloe vera gel has been used for centuries by those living where the plant naturally grows as a health and beauty aid.

For example, Aloe vera is a traditional anti-inflammatory topical ointment used to combat the inflammation and pain caused by jelly fish stings, insect bites, sunburn and the like. Aloe vera soothes and cools the inflamed skin, numbs the pain associated with the inflammation and prevents itching.

Aloe vera is a traditional remedy for many digestive disorders such as irritable bowel syndrome, ulcerative colitis, Crohn's disease, oesophagitis, peptic ulcers and oral lesions. Additionally, as an abundant source of essential nutrients, Aloe vera is a nutritional supplement and a detoxifying tonic that revitalizes the body. Moreover, as a beauty aid, Aloe vera enhances the ability of the skin to absorb moisture, thus revitalizing the skin.

The therapeutic qualities of the clear gel of the Aloe vera plant described above depend on the freshness of the gel. For example, the pain of a sunburn may be stopped, not to reoccur, by applying the clear gel from a leaf that has just been cut, but if the gel has been exposed to air and light for several hours the therapeutic powers are partially lost.

Several processes have been developed and are employed to preserve the freshness and therapeutic qualities of the Aloe vera gel. For example, FIG. 1 depicts a prior art process 10 for preserving the freshness and therapeutic qualities of the Aloe vera gel. The Aloe vera gel is heated to 49° C. at step 12. At step 14, ascorbic acid is added. At step 16, the Aloe vera gel is cooled to about 25° C. The existing processes, such as process 10 of FIG. 1, however, cannot meet the demands of today's marketplace.

The beneficial properties of the Aloe vera plant have created a demand for Aloe vera gel and Aloe vera products in regions where Aloe vera may not be grown. Thus, the market area for Aloe vera gel has expanded far from Aloe vera sources and the distance to the marketplaces has greatly increased. Accordingly, Aloe vera gel is delivered to the marketplaces by transcontinental transport, such as by truck or train, and by transoceanic transport, such as by ship. Environmental control during transcontinental and transoceanic transport is difficult. Environmental conditions, such as light, temperature, and humidity are extreme and place a great stress on the Aloe vera gel. Moreover, production of Aloe vera products in large quantities translates into longer storage times, and therefore, a need for products with longer shelf-lives.

The greater demand for Aloe vera in more remote marketplaces requires an Aloe vera gel with a stability that the existing stabilizing processes cannot provide. Accordingly, a need exists for a stabilizing process and a resulting Aloe vera gel that retains its beneficial properties while experiencing the extreme environmental conditions of transcontinental and transoceanic transport. Moreover, a need exists for an Aloe vera gel with a significantly increased shelf life. The present invention provides such a process and gel.

SUMMARY OF THE INVENTION

The present invention disclosed herein comprises a product and process for stabilizing Aloe vera gel. In one aspect, the present invention is directed to a process for stabilizing Aloe vera gel that comprises the steps of heating the Aloe vera gel to a temperature in the range of from about 35° C. to about 80° C., adding to the heated Aloe vera gel a tocotrienol/tocopherol blend in an amount from about 0.01% to about 2.0% based on the weight of the Aloe vera gel, and cooling the heated Aloe vera gel to a temperature in the range of from about 20° C. to about 30° C. The process may further comprise the step of adding rosmarinic acid in an amount from about 0.01% to about 0.5% based on the weight of the Aloe vera gel. The process may further comprise the step of adding polyphenols in an amount from about 0.01% to about 0.7% based on the weight of the Aloe vera gel.

In another aspect, the present invention is directed to a process for stabilizing Aloe vera gel that comprises the steps of heating the Aloe vera gel to a temperature in the range of from about 35° C. to about 80° C., adding to the heated Aloe vera gel rosmarinic acid in an amount from about 0.01% to about 0.5% based on the weight of the Aloe vera gel, and cooling the heated Aloe vera gel to a temperature in the range of from about 20° C. to about 30° C. The process may further comprise the step of adding polyphenols in an amount from about 0.01% to about 0.7% based on the weight of the Aloe vera gel.

In another aspect of the invention, the present invention is directed to a process for stabilizing Aloe vera gel that comprises the steps of heating the Aloe vera gel to a temperature in the range of from about 35° C. to about 80° C., adding to the heated Aloe vera gel polyphenols in an amount from about 0.01% to about 0.7% based on the weight of the Aloe vera gel, and cooling the heated Aloe vera gel to a temperature in the range of from about 20° C. to about 30° C. The process may further comprise the step of adding a tocotrienol/tocopherol blend in an amount from about 0.01% to about 2.0% based on the weight of the Aloe vera gel.

Any of aforementioned processes may further comprise the step of adding ascorbic acid in the amount from about 0.05% to about 1.0% based on the weight of the Aloe vera gel. Additionally, the processes may include the step of adding at least one stabilizing agent in an amount from about 0.01% to about 6.0% based on the weight of the Aloe vera gel. The stabilizing agent may be sodium benzoate, citric acid, potassium sorbate, phosphoric acid, glucono-deltalactone, or any combination thereof. The heated Aloe vera gel may be mixed during the process to insure a homogeneous mixture. The product may be produced by any of aforementioned processes.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figure 1:
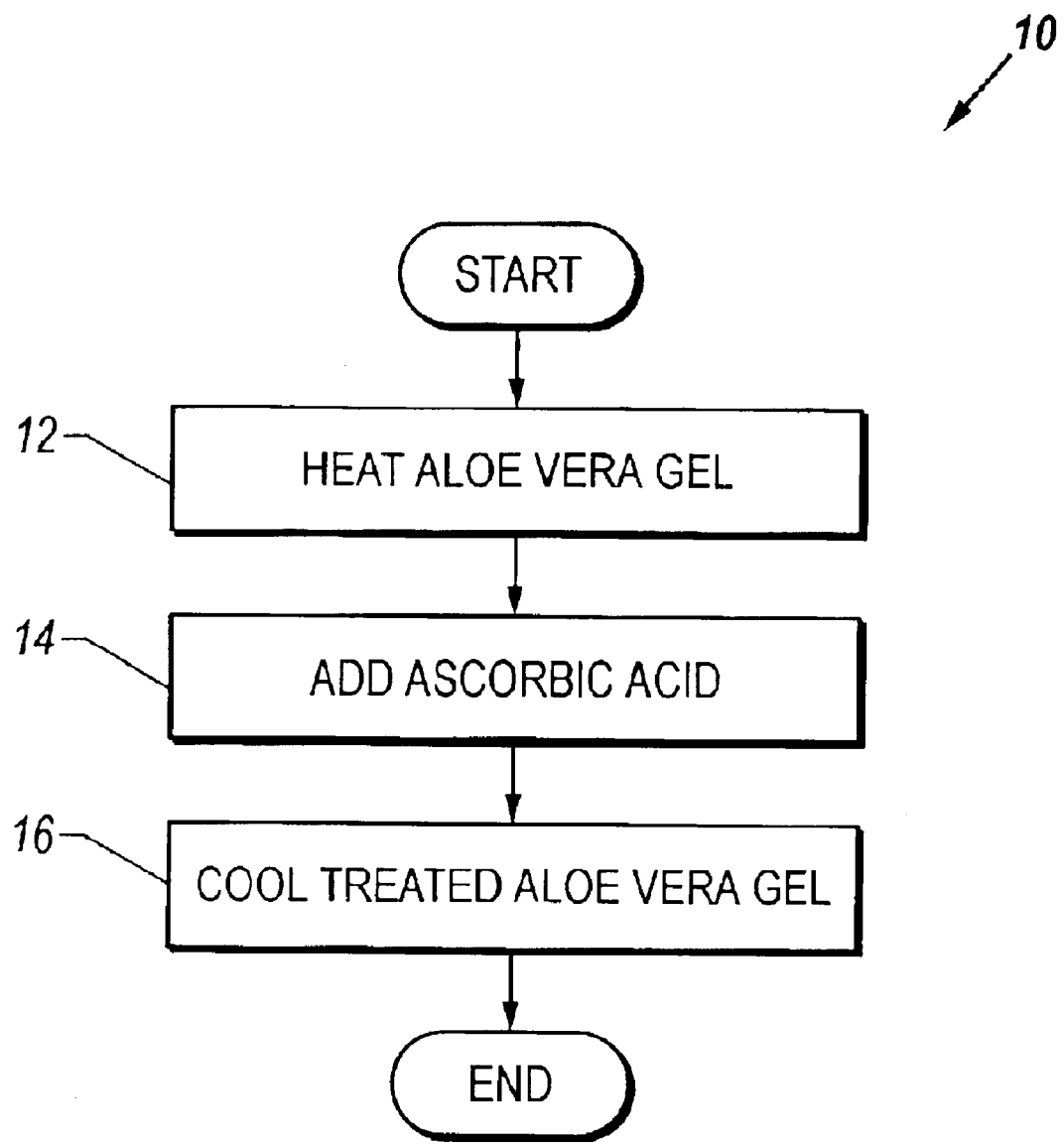
FIG. 1 (Prior Art) depicts a flow chart of a prior art process for preserving Aloe vera gel.
Figure 2A:
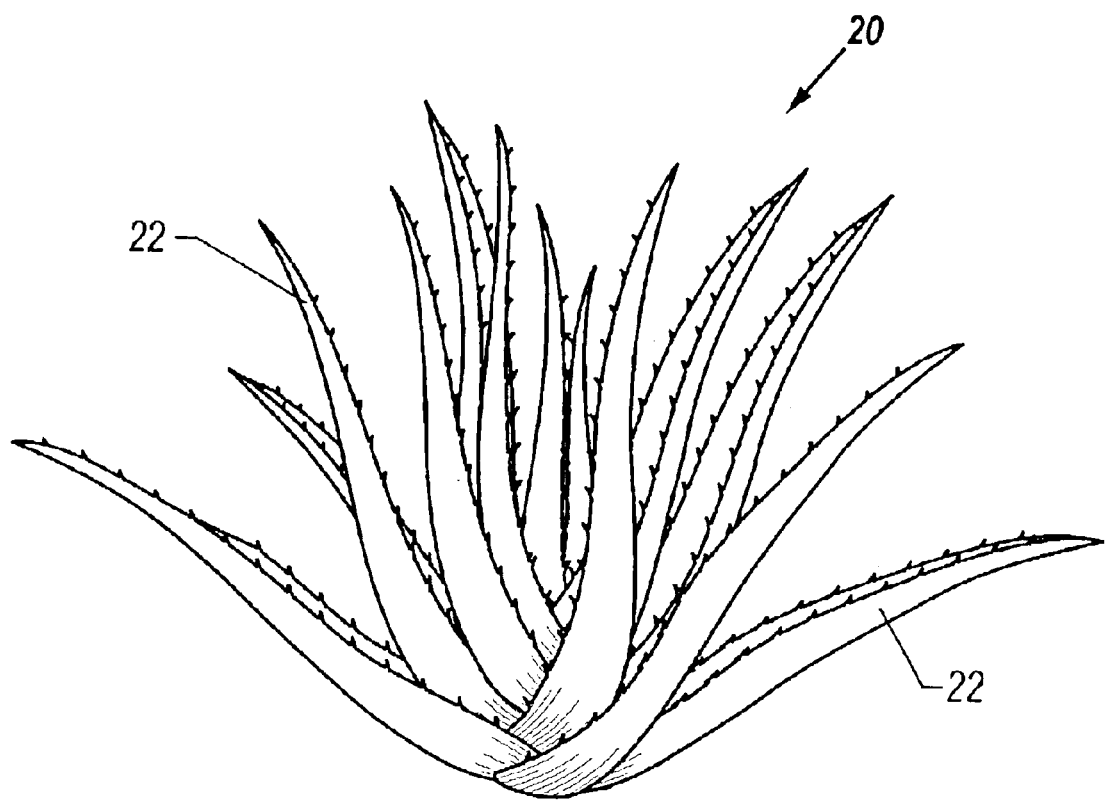
FIG. 2A (Prior Art) depicts a front view of an Aloe vera plant.
Figure 2B:
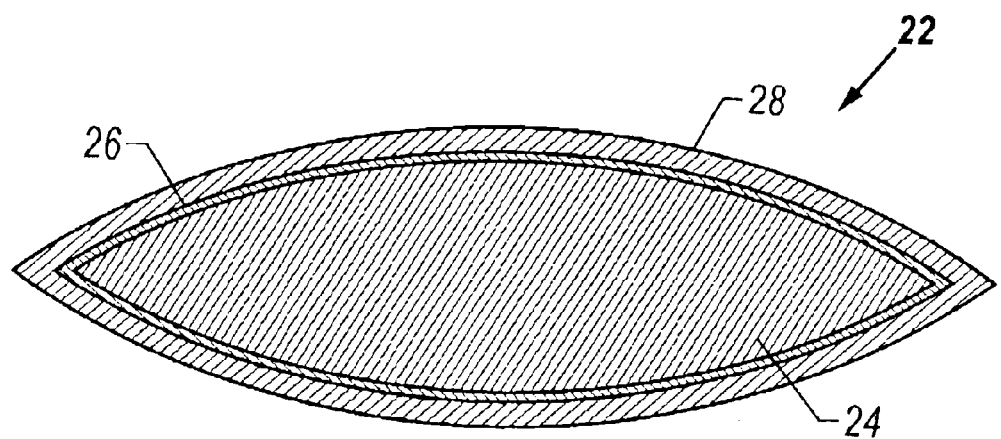
FIG. 2B (Prior Art) depicts a cross-sectional view of a leaf of the Aloe vera plant of FIG. 2A.

Referring initially to FIG. 2A, a front view of a fully mature Aloe vera plant, *Aloe barbadensis*, is illustrated and generally designated 20. Leaves 22 grow in a spiral rosette pattern around a central stem. FIG. 2B depicts a cross-sectional view of a leaf 22. The leaf contains the Aloe vera gel 24 which, as discussed, has numerous beneficial properties. The Aloe vera gel is a viscous, translucent, mucilaginous gel containing various polysaccharides that are believed to be largely responsible for Aloe vera's beneficial properties. The Aloe vera gel is housed in an interior layer 26 comprising vascular bundles or tubes that include pericyclic tubes. These hair-like connective fibers provide rigidity to the plant. A thick outer rind 28 surrounds and protects the interior layer and the Aloe vera gel.

The leaves are harvested when the plant is fully mature. A fully matured plant, preferably four to five years in age, has broader leaves than that of a plant that has not yet reached maturity. Accordingly, the leaves of a fully matured Aloe vera plant contain a larger amount of Aloe vera gel than immature plants.

It is preferable that the leaves be processed immediately after cutting, because degradable decomposition of the gel begins upon cutting due to enzymatic reactions and the activity of bacteria normally present in the leaves. After the leaves are cut, they are carefully washed with clean water and are preferably soaked for about five minutes in a suitable non-irritative bactericide and fungicide.

The Aloe vera gel may be extracted from the leaves either by a "filet" method or a "whole-leaf" method. In the preferred embodiment of the present invention, the filet method is employed. In this method, the anthraquinone-containing yellow sap from the pericyclic cells is drained from the freshly-cut leaves, then collected and discarded. Before further processing, the Aloe vera leaves are washed with clean water and soaked for several minutes in a water bath containing a suitable bactericide/fungicide. The leaves are then rinsed, the tips and bases are cut off, and the filet gel is extracted from the leaves. The fresh gel is then collected and any foreign particles are separated from the gel manually.

In the whole leaf method, the Aloe vera leaves including the rinds are cut into sections and then ground into a slurry. Preferably, the slurry is subjected to a chemical process to break down the hexagonal structure of the Aloe vera leaf. The treated slurry is passed through a series of coarse screening filters to remove large foreign particles.

While initially it was thought that the whole-leaf process provided a product that contained more of the active polysaccharides, it is now believed that the Aloe vera gel extracted from the interior of the leaves provides a higher concentration of polysaccharides. Thus, the preferred method of the present invention employs the filet method rather than the whole leaf method. However, it should be understood by one skilled in the art that the present invention may be used with either Aloe vera gel obtained by the whole leaf method or filet method.

The Aloe vera gel, whether obtained by the filet method, whole-leaf method, or another method, is transferred to a mixing vessel equipped for temperature control. Preferably the mixing vessel and equipment are made of stainless steel to minimize contamination of the product.

Figure 3A:
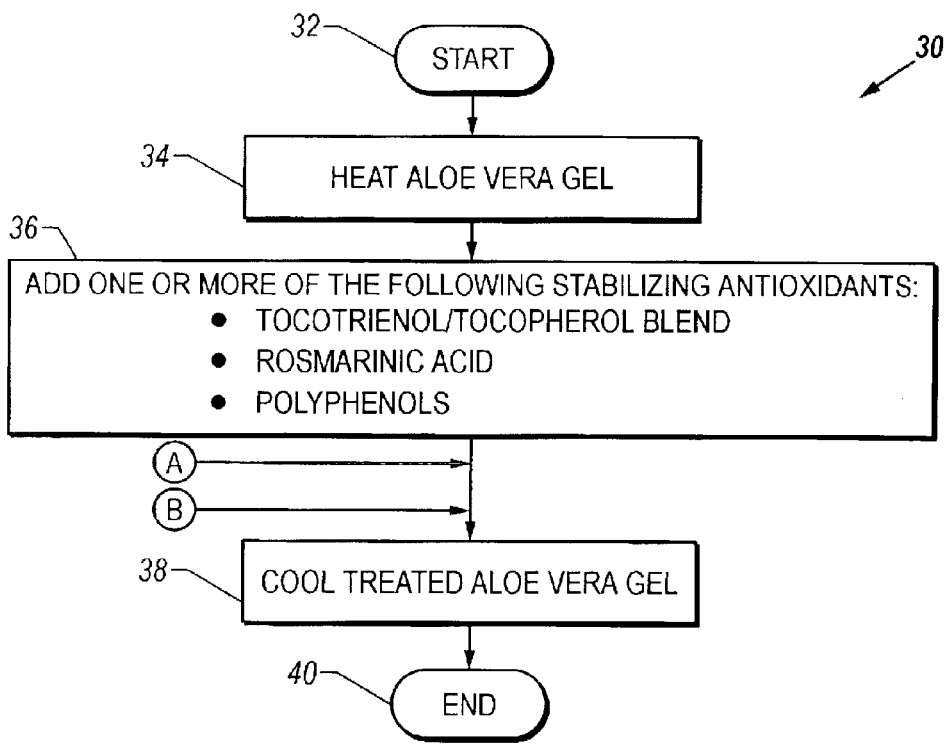
FIG. 3A depicts a flow chart of a presently preferred exemplary process of the present invention for stabilizing Aloe vera gel.

Referring now to FIG. 3A, wherein a flow chart depicts a presently preferred exemplary process 30 for stabilizing Aloe vera gel. After the Aloe vera gel has been introduced into the mixing vessel, the Aloe vera gel is ready for a high temperature, short time (HTST) treatment process (step 32). At step 34, the Aloe vera gel is mixed and quickly heated to a temperature in a range of from about 35° C. to about 80° C. and preferably in the range from about 60° C. to about 75° C. for a period of time sufficient to kill bacteria which may be present. The temperature of the Aloe vera gel is then quickly lowered to about 50° C.

At step 36, one or more stabilizing antioxidant agents, namely a tocotrienol/tocopherol blend, rosmarinic acid, and/or polyphenols, are added to the Aloe vera gel to impart stability. Preferably, all three stabilizing antioxidants are added. The temperature is maintained at about 50° C. and the mixture is stirred for a suitable amount of time to insure a homogeneous mixture as each of the one or more stabilizing antioxidant agents is added.

In a presently preferred exemplary embodiment, the tocotrienol/tocopherol blend is added in an amount from about 0.01% to about 2.0% based on the weight of the Aloe vera gel. All percentages presented hereinafter are based on the weight of the Aloe vera gel. More preferably, the tocotrienol/tocopherol blend is added in the amount from about 0.01% to about 0.5%.

The tocotrienol/tocopherol blend comprises at least one of the following: alpha tocotrienol, beta tocotrienol, gamma tocotrienol, or delta tocotrienol. The structural name for alpha tocotrienol is 2,5,7,8-tetramethyl-2-(4"8"12"-trimethyltrideca-3"7"11"-trienyl)-6-chromanol. Additionally, the tocotrienol/tocopherol blend comprises at least one of the following: alpha-tocopherol, beta-tocopherol, gamma-tocopherol, or delta-tocopherol. The structural name for alpha-tocopherol is 2,5,7,8-tetramethyl-2-(4"8"12"-trimethyltridecyl)-6-chromanol. Preferably, the tocotrienol/tocopherol blend comprises at least 25 IU/gram of gamma-tocotrienol). A suitable tocotrienol/tocopherol blend may be obtained from extracted and concentrated rice bran oil distillate. A presently preferred tocotrienol/tocopherol blend is marketed under the name NUTRIENE® by Eastman Chemical Co. of Kingsport, Tenn.

In a presently preferred exemplary embodiment, rosmarinic acid, $C_{18}O_8H_{16}$, is added in an amount from about 0.01% to about 0.5%. More preferably, rosmarinic acid is added in the amount from about 0.01% to about 0.25%. Rosmarninic acid may be derived from edible herbs belonging to the Labiatae family such as the herb rosemary. A suitable blend containing a high concentration of rosmarinic acid is marketed under the name Origanox™ by the Israel-based company RAD Natural Technologies. Pure rosmarinic acid may be obtained from a variety of companies including CMS Chemicals Limited of Oxfordshire, United Kingdom.

In a presently preferred exemplary embodiment, polyphenols are added in an amount from about 0.01% to 0.7%. More preferably, polyphenols are added in the amount from about 0.05% to 0.25%. Polyphenols refer to a class of chemicals also known as polymeric phenols. Preferably, the polyphenols comprise one or more of the following chemicals: a procyanidin, a proanthocyanidin, a cinnamic acid, such as caftaric acid (3-deoxycaftaric acid), or a phenolic acid, such as gallic acid. Polyphenols may be derived from grapes or green tea. A suitable source of polyphenols is the polyphenol blend available under the name MEGANATURAL® (Polyphenolics, Inc. of Madera, Calif.), which is at least 80% polyphenols.

At step 38, the treated Aloe vera gel is rapidly cooled by employing a heat exchanger to a temperature between about 20° C. to about 30° C. At step 40, the process is complete and the stabilized Aloe vera gel may then be packaged and transported to marketplaces far away.

Figure 3B:
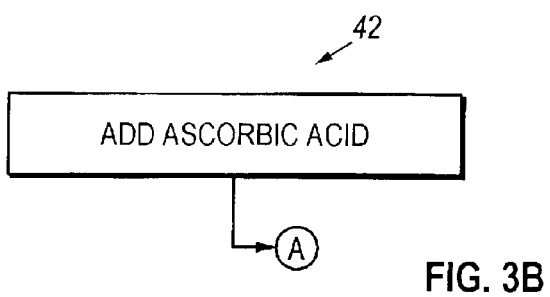
FIG. 3B depicts a first optional step that can be added to the presently preferred process of FIG. 3A.

Referring now to FIG. 3B, after one or more of the following stabilizing antioxidants is added at step 36, ascorbic acid may be added in an amount from about 0.05% to about 1.0% (step 42) to further retard oxidation.

Figure 3C:
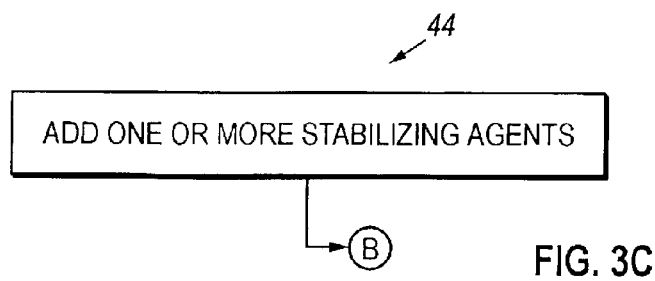
FIG. 3C depicts a second optional step that can be added to the presently preferred process of FIG. 3A.

Referring to FIG. 3C, at step 44, in a presently preferred embodiment, prior to cooling the treated Aloe vera gel at step 38 and while maintaining the temperature at the predetermined temperature with continued agitation, one or more of the following stabilizing agents may be added to the treated Aloe vera gel (all percentages are based on the weight of Aloe vera gel):

sodium benzoate in an amount from about 0.05% to about 0.5%, citric acid in an amount from about 0.01% to about 0.5%, potassium sorbate in an amount from about 1.0% to about 6.0%, phosphoric acid in an amount from about 0.01% to about 0.5%, or glucono-delta-lactone in an amount from about 0.01% to about 1.0%.

After the process 30 is complete and the Aloe vera gel has been transported, the stabilized Aloe vera gel may be bottled as a beverage (with or without flavoring), exposed to further molecular size exclusion processes for use in either cosmetics or over-the-counter drug products, or stored for later use. The stabilized Aloe vera gel produced by the processes of the present invention exhibits a substantially improved shelf life over Aloe vera gel products produced by existing methods. Moreover, the stabilized Aloe vera gel produced by the process of the present invention exhibits greater stability when subjected to the uncontrolled environmental conditions of transcontinental and transoceanic transport over Aloe vera gel products produced by existing methods.

EXAMPLE

The following example is presented to explain in more detail the advantages of different embodiments of the present invention. Accordingly, it is not to be interpreted in a limiting fashion.

Mature Aloe vera leaves were harvested and the Aloe vera gel was immediately processed by the filet method described previously. The Aloe vera gel was then divided into eight batches. While the Aloe vera gel was being processed, the following eight treatments were prepared (all percentages presented are based on the weight of the Aloe vera gel):

| Treatment | Composition |
| --- | --- |
| Treatment A | 0.5% ascorbic acid |
| Treatment B | 0.20% NUTRIENE ® tocotrienol/tocopherol blend |
| Treatment C | 0.20% ORIGANOX ™ rosmarinic acid edible herb derivative |
| Treatment D | 0.20% MEGANATURAL ® polyphenol |
| Treatment E | a homogenous mixture of 0.20% sodium benzoate, 0.10% citric acid, 1.0% potassium sorbate, 0.20% phosphoric acid, and 0.20% glucono-delta-lactone |
| Treatment F | a homogenous mixture of Treatment A and E |
| Treatment G | a homogenous mixture of Treatments B, C, and D |
| Treatment H | a homogenous mixture of Treatments B, C, D, E, and F |

Each of the eight batches of the freshly-processed aloe vera gel was placed into a separate temperature-controlled mixing vessel and heated quickly to 75° C., for a short period of time, and then rapidly cooled to 50° C. Each batch was then treated with one of the eight treatments (Treatments A–H), mixed to achieve homogeneity, and quickly cooled to about ambient temperature.

Stability testing was then conducted on each of the eight batches (Batches A–H). Samples from each batch were stored at 45° C. and 75% relative humidity, and periodically tested for the relevant parameters (color, odor, pH, taste, etc.) to determine stability. The following table describes the results:

| Batch | Stability |
| --- | --- |
| Batch A | degraded after 1 month |
| Batch B | degraded after 3 months |
| Batch C | degraded after 3.25 months |
| Batch D | degraded after 3.25 months |
| Batch E | degraded after 2 months |
| Batch F | degraded after 2.25 months |
| Batch G | did not degrade after 4 months |
| Batch H | did not degrade after 4 months |

Batch A, Aloe vera gel stabilized by an existing process, degraded after one month of testing. The stabilized Aloe vera gels prepared by the processes of the present invention, Batches B, C, D, E, F, G, and H, exhibited improved stability. The stabilized Aloe vera gel of the present invention demonstrated at least twice the stability of Aloe vera gel stabilized according to existing processes.

The stabilized aloe vera gel of the present invention demonstrates substantially improved shelf life when subjected to harsh environmental conditions. In this capacity, the ability of the stabilized Aloe vera gel of the present invention to remain stable when subjected to the uncontrolled environmental conditions of transcontinental and transoceanic transport is especially useful.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A process for stabilizing Aloe vera gel comprising:
    heating the Aloe vera gel to a temperature in the range of from about 350° C. to about 80° C.;
    adding to the heated Aloe vera gel a compound in an amount from about 0.01% to about 0.7% based on the weight of the Aloe vera gel, the compound being selected from the chemical group consisting of procyanidin, proanthocyanidin, cinnamic acid, caftaric acid (3-deoxycaftaric acid), phenolic acid, and gallic acid; and
    cooling the heated Aloe vera gel to a temperature in the range of from about 20° C. to about 30° C.
2. The product produced by the process of claim 1.
3. The process as recited in claim 1, wherein the step of heating the Aloe vera gel to a temperature in the range of from about 35° C. to about 80° C. further comprises heating the Aloe vera gel to a temperature in the range of from about 60° C. to about 75° C.
4. The process as recited in claim 1, further comprising the step of adding to the heated Aloe vera gel a tocotrienol/tocopherol blend in an amount from about 0.01% to about 2.0% based on the weight of the Aloe vera gel.
5. The product produced by the process of claim 4.
6. The process as recited in claim 1, further comprising the step of adding to the heated Aloe vera gel ascorbic acid in an amount from about 0.05% to about 1.0% based on the weight of the Aloe vera gel.
7. The product produced by the process of claim 6.
8. The process as recited in claim 1, further comprising the step of adding to the heated Aloe vera gel at least one stabilizing agent in an amount from about 0.01% to about 6.0% based on the weight of the Aloe vera gel, the at least one stabilizing agent selected from the group consisting of sodium benzoate, citric acid, potassium sorbate, phosphoric acid, and glucono-delta-lactone.
9. The product produced by the process of claim 8.
10. The process as recited in claim 1, further comprising the step of deriving the compound from green tea.
11. The process as recited in claim 1, further comprising the step of deriving the compound from grapes.
12. A process for stabilizing Aloe vera gel comprising:
    heating the Aloe vera gel to a temperature in the range of from about 35° C. to about 80° C.;
    adding to the heated Aloe vera gel procyanidin in an amount from about 0.05% to about 0.25% based on the weight of the Aloe vera gel; and
    cooling the heated Aloe vera gel to a temperature in the range of from about 20° C. to about 30° C.
13. The product produced by the process of claim 12.
14. A process for stabilizing Aloe vera gel comprising:
    heating the Aloe vera gel to a temperature in the range of from about 35° C. to about 80° C.;
    adding to the heated Aloe vera gel proanthocyanidin in an amount from about 0.05% to about 0.25% based on the weight of the Aloe vera gel; and
    cooling the heated Aloe vera gel to a temperature in the range of from about 20° C. to about 30° C.
15. The product produced by the process of claim 14.
16. A process for stabilizing Aloe vera gel comprising:
    heating the Aloe vera gel to a temperature in the range of from about 35° C. to about 80° C.;
    adding to the heated Aloe vera gel cinnamic acid in an amount from about 0.05% to about 0.25% based on the weight of the Aloe vera gel; and
    cooling the heated Aloe vera gel to a temperature in the range of from about 20° C. to about 30° C.
17. The product produced by the process of claim 16.
18. A process for stabilizing Aloe vera gel comprising:
    heating the Aloe vera gel to a temperature in the range of from about 35° C. to about 80° C.;
    adding to the heated Aloe vera gel caftaric acid (3-deoxycaftaric acid) in an amount from about 0.05% to about 0.25% based on the weight of the Aloe vera gel; and
    cooling the heated Aloe vera gel to a temperature in the range of from about 20° C. to about 30° C.
19. The product produced by the process of claim 18.
20. A process for stabilizing Aloe vera gel comprising:
    heating the Aloe vera gel to a temperature in the range of from about 35° C. to about 80° C.;
    adding to the heated Aloe vera gel phenolic acid in an amount from about 0.05% to about 0.25% based on the weight of the Aloe vera gel; and
    cooling the heated Aloe vera gel to a temperature in the range of from about 20° C. to about 30° C.
21. The product produced by the process of claim 20.
22. A process for stabilizing Aloe vera gel comprising:
    heating the Aloe vera gel to a temperature in the range of from about 35° C. to about 80° C.;
    adding to the heated Aloe vera gel gallic acid in an amount from about 0.05% to about 0.25% based on the weight of the Aloe vera gel; and
    cooling the heated Aloe vera gel to a temperature in the range of from about 20° C. to about 30° C.
23. The product produced by the process of claim 22.

* * * * *